United States Patent
Rollat et al.

(10) Patent No.: US 6,346,234 B1
(45) Date of Patent: Feb. 12, 2002

(54) HAIR STYLING COMPOSITION CAPABLE OF BEING REMODELLED WITH A TG OF LESS THAN +10 °C

(75) Inventors: Isabelle Rollat, Boulogne; Christine Dupuis, Paris; Henri Samain, Bièvres, all of (FR)

(73) Assignee: L'Oreal, S.A., Paris (FR)

( * ) Notice: Subject to any disclaimer, the term of this patent is extended or adjusted under 35 U.S.C. 154(b) by 0 days.

(21) Appl. No.: 09/380,467

(22) PCT Filed: Mar. 2, 1998

(86) PCT No.: PCT/FR98/00403

§ 371 Date: Oct. 29, 1999

§ 102(e) Date: Oct. 29, 1999

(87) PCT Pub. No.: WO98/38969

PCT Pub. Date: Sep. 11, 1998

(30) Foreign Application Priority Data

Mar. 4, 1997 (FR) .............................. 97 02558

(51) Int. Cl.⁷ .............................. A61K 7/06; A61K 7/00
(52) U.S. Cl. ...................... 424/47; 424/70.1; 424/70.11
(58) Field of Search .............................. 424/481, 47, 45, 424/43, 70.1, 70.11

(56) References Cited

U.S. PATENT DOCUMENTS

| | | |
|---|---|---|
| 3,546,008 A | 12/1970 | Shields et al. |
| 3,734,874 A | 5/1973 | Kibler et al. |
| 3,779,993 A | 12/1973 | Kibler et al. |
| 3,836,537 A | 9/1974 | Boerwinkle et al. |
| 4,223,196 A | 9/1980 | Erlandson et al. |
| 4,340,519 A | 7/1982 | Kotera et al. |
| 4,525,524 A * | 6/1985 | Tung et al. |
| 5,386,003 A | 1/1995 | Greene et al. |
| 5,441,728 A * | 8/1995 | Tsaur et al. |

FOREIGN PATENT DOCUMENTS

| | | |
|---|---|---|
| EP | 0 320 218 | 6/1989 |
| EP | 0 524 346 | 1/1993 |
| EP | 0 758 545 | 2/1997 |
| EP | 0 758 546 | 2/1997 |
| EP | 0 764 437 | 3/1997 |
| FR | 1 400 366 | 12/1965 |
| FR | 2 737 660 | 2/1997 |
| WO | 91/15186 | 10/1991 |
| WO | 92/16179 | 10/1992 |
| WO | 95/32997 | 12/1995 |
| WO | 97/09030 | 3/1997 |
| WO | 97/29734 | 8/1997 |
| WO | 97/33558 | 9/1997 |

OTHER PUBLICATIONS

English language Derwent Abstract of EP 0 758 545, (1997).
English language Derwent Abstract of EP 0 758 546, (1997).
English language Derwent Abstract of EP 0 764 437, (1997).
English language Derwent Abstract of FR 2 737 660, (1997).

* cited by examiner

Primary Examiner—Brian K. Seidleck
(74) Attorney, Agent, or Firm—Finnegan, Henderson, Farabow, Garrett & Dunner, L.L.P.

(57) ABSTRACT

The invention concerns a hairstyling composition capable of being remodelled for keratin fibers in particular hair, containing in an appropriate cosmetic vehicle at least a polymer selected such that the composition, after being applied on the fibers and dried, provides a hairstyling substance having a glass temperature (Tg) less than +10° C. and a separation profile defined by at least: (a) a maximum separation force $F_{max} > 1$ Newton and (b) when said glass temperature Tg is less than $-15°$ C., by a separation energy $E_{s(M/V)}$ of the substance contacted with a glass surface, less than 300 µJ. The invention also concerns an aerosol device containing this composition and a method for treating keratin fibers such as hair, in particular a method for fixing and/or maintaining the hairstyle using said composition.

41 Claims, No Drawings

HAIR STYLING COMPOSITION CAPABLE OF BEING REMODELLED WITH A TG OF LESS THAN +10 °C

This application is a 371 of PCT/FR98/00403, filed Mar. 2, 1998.

The present invention relates to a remodellable hair Styling composition which allows the hairstyle to be modified while retaining its shape and without having to rewet the hair or heat it excessively. It also relates to a device which is particularly suitable for dispensing the composition according to the invention. Finally, it relates to a method of treating keratinous fibres, especially hair, for which the composition according to the invention is applied to the said fibres.

Fixing the hairstyle is an important element in hair styling, and consists in maintaining the shaping which has already been carried out or in simultaneously shaping and fixing the hair.

The most widespread hair products on the cosmetics market for shaping and/or maintaining the hairstyle are spray compositions consisting essentially of a solution, usually alcohol- or water-based, and one or more materials, generally polymer resins, whose function is to form links between the hairs, these materials also being called fixatives, in a mixture with various cosmetic adjuvants. This solution is generally packaged either in an appropriate aerosol container, which is pressurized with the aid of a propellant, or in a pump flask.

Also known are styling gels or mousses, which are generally applied to the wetted hair before brushing or setting it. In contrast to the conventional aerosol lacquers, these compositions have the disadvantage that they do not allow the hair to be fixed in a shape brought about beforehand. In fact, these compositions are essentially aqueous, and their application wets the hair and is therefore unable to maintain the initial shape of the hairstyle. In order to shape and fix the hairstyle, therefore, it is necessary to carry out subsequent brushing or drying.

The prior art compositions all have the same disadvantage that they do not allow the hairstyle to be modified to a desired shape which is other than that formed initially, without starting the styling and fixing operations again. Furthermore, under any kind of stress, the hairstyle has a tendency to take on an undesirable permanent set which cannot easily be modified.

Patent application EP 524 346 discloses a composition that makes it possible to obtain a hairstyle which can be modified after setting. However, in order to be able to modify the hairstyle, it is necessary to heat it to a temperature greater than the glass transition temperature (Tg) of the fixative material, which may be up to 120° C.

The Applicant has now found that, by selecting certain suitable polymers, alone or in combination with certain additives in an appropriate, cosmetically acceptable vehicle, it is possible to obtain remodellable hair styling; that is, to obtain a specific styling material which enables the hairstyle to be modified while preserving its shape, without having to rewet the hair or heat it excessively.

The styling materials suitable for obtaining this remodellable hair styling effect according to the invention must on the one hand, following application to the substrate and drying, have a glass transition temperature (Tg) of less than +10° C.

On the other hand, following application to the substrate and drying, they must exhibit a detachment profile defined by at least:

(a) a maximum detachment force $F_{max}$>1 newton and
(b) when the glass transition temperature (Tg) is lower than −15° C., by a separation energy $E_{s(m/g)}$ of the material placed in contact with a glass surface of less than 300 µJ.

According to the present invention, Fmax denotes the maximum tensile force, measured using an extensometer, required to detach the respective 38 mm² surfaces of two rigid, inert and non-absorbent substrates (A) and (B) placed opposite one another, the said surfaces being coated beforehand with the said composition at a rate of 53/c µg/mm², c being the dry matter concentration in the composition (in grams per gram of composition), i.e. the ratio of the mass of dry matter in the composition to the total mass of the composition, and the said surfaces being dried for 24 hours at 22° C. and a relative humidity of 50%, then subjected for 20 seconds to a compressive force of 3 newtons and finally subjected for 30 seconds to tension at a rate of 20 mm/minute.

According to the present invention, $E_{s(m/g)}$ denotes the energy supplied by the extensometer in order to bring about the "separation" of the respective 38 mm² surfaces of two rigid, inert and non-absorbent substrates (C) and (D) placed opposite one another; one of the said substrates consisting of polished glass and the other of the said substrates being identical in nature to the above-defined substrates (A) and (B) and having a surface which is coated with the composition at a rate of 53/c µg/mm², c being the dry matter concentration in the composition (in grams per gram of composition), i.e. the ratio of the mass of dry matter in the composition to the total mass of the composition, and dried for 24 hours at 22° C. and a relative humidity of 50%; the two surfaces of the said substrates (C) and (D) being subjected subsequently for 20 seconds to a compressive force of 3 newtons and finally subjected for 30 seconds to tension at a rate of 20 mm/minute.

This energy provided by the extensometer is the work calculated using the following formula:

$$\int_{x_{s1}+0.05}^{x_{s2}} F(x)dx$$

where F(x) is the force required to produce a displacement (x);

$X_{s1}$ is the displacement (in millimeters) produced by the maximum tensile force;

$X_{s2}$ is the displacement (in millimeters) produced by the tensile force which permits the total separation of the two surfaces of the above-defined substrates (C) and D).

The present invention therefore provides a remodellable hair styling composition comprising, in a cosmetic vehicle suitable for keratinous fibres, and more particularly for hair, at least one polymer selected such that, following application to the fibres and drying, it leads to a styling material as defined above.

According to the present invention, glass transition temperature (Tg) denotes the Tg of the styling material obtained following application of the composition to the substrate and drying, with the exception of volatile materials that may be present. The glass transition temperature is determined by DSC (calorimetric method).

By styling material there will be understood, throughout the description, any material which allows the desired remodellable styling effect to be obtained.

Preferentially, the styling material consists essentially of at least one fixative polymer, alone or in combination with conventional cosmetic additives, for example plasticizers, or neutralizing agents.

In accordance with the invention it is possible to use any fixative polymer which is known per se, provided that the Tg of the styling material obtained is less than +10° C. and meets the adhesiveness conditions as indicated above.

Where the styling material consists of a mixture of polymers and other constituents, it is not necessary for the Tg of each of the polymeric constituents to be less than +10° C., since there are numerous possibilities for adjusting the Tg by means of blends (blends of polymers, plasticizers).

Use may be made in particular of fixative polymers selected from anionic, cationic, amphoteric and non-ionic polymers and mixtures thereof. The fixative polymer may additionally be halogenated, in particular fluorinated.

The fixative polymers can be used in solubilized form or else in the form of dispersions of solid polymer particles (latex or pseudo-latex).

The cationic fixative polymers which can be used according to the present invention are preferably selected from polymers containing primary, secondary, tertiary and/or quaternary amine groups forming part of the polymer chain or linked directly to it and having a molecular weight of between 500 and approximately 5,000,000 and preferably between 1000 and 3,000,000.

The anionic fixative polymers that are generally used are polymers containing groups derived from carboxylic, sulphonic or phosphoric acid and have a weight-average molecular weight of between approximately 500 and 5,000,000.

Anionic fixative polymers Which are particularly preferred according to the invention are the sulphonated polyesters comprising repeating units representable by the following general formula:

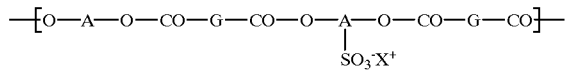

in which A and G represent divalent radicals and X represents an alkali metal, especially sodium or potassium. Among the preferred sulphonated polyesters according to the invention, A represents an arylene radical, especially phenylene, and G represents a linear or branched alkylene radical optionally interrupted by one or more oxygen atoms, or a cycloalkylene radical. When G represents a linear or branched alkylene radical optionally interrupted by one or more oxygen atoms, the radical —O—G—O— is preferably a (poly)alkylene glycol residue containing 1 to 20 alkylene glycol units. The alkylene radical is preferably, according to the invention, a lower, linear or branched $C_2$–$C_4$ alkylene radical, more preferably an ethylene radical. Such polymers are described in particular in the patents U.S. Pat. No. 3,546,008, U.S. Pat. No. 4,340,519, U.S. Pat. No. 3,734,874, U.S. Pat. No. 3,779,993, U.S. Pat. No. 4,233,196 and U.S. Pat. No. 5,386,003 and in the patent application WO 95/32997. Among these polymers, preference will be given to those marketed under the names AQ 1045, AQ 1350 and AQ 14000 by the company EASTMAN CHEMICAL, more particularly AQ 1350.

The amphoteric fixative polymers which can be used in accordance with the invention can be selected from polymers comprising units B and C distributed randomly in the polymer chain, where B denotes a unit deriving from a monomer containing at least one basic function, in particular a basic nitrogen atom, and C denotes a unit deriving from an acidic monomer containing one or more carboxyl or sulpho groups, or else B and C can denote groups deriving from zwitterionic carboxybetaine or sulphobetaine monomers; B and C may also denote a cationic polymer chain containing primary, secondary, tertiary or quaternary amine groups, in which at least one of the amine groups carries a carboxyl or sulpho group linked by way of a hydrocarbon radical, or else B and C form part of a chain of a polymer having an $\alpha,\beta$-dicarboxy ethylene unit in which one of the carboxyl groups has been reacted with a polyamine containing one or more primary or secondary amine groups. Such amphoteric polymers are described, in particular, in the patents and patent applications U.S. Pat. No. 3,836,537 and FR 1,400,366.

The anionic or amphoteric fixative polymers can, if required, be partly or totally neutralized. The neutralizing agents are, for example, sodium hydroxide, potassium hydroxide, 2-amino-2-methyl-1-propanol, monoethanolamine, triethanolamine or triisopropanolamine, or organic or inorganic acids, such as hydrochloric acid or citric acid.

The non-ionic fixative polymers useful according to the present invention are, in particular, polyurethanes.

The conditions relating to the detachment profile of the styling material of the invention can be measured and calculated in accordance with the following procedures:

Procedure Relating to the Measurement of Fmax

The maximum tensile force $F_{max}$ required to separate two surfaces of two rigid, inert and non-absorbent substrates, placed opposite one another and coated with the styling material to be evaluated, is determined using an extensometer, for example an apparatus of the LLOYD model LR5K type.

The solid, rigid, inert and non-absorbent substrates can be selected from those consisting of polyethylene, polypropylene, metal alloy and, more preferably, glass.

For the substrates it is preferred to use a pair of blocks consisting of a glass disc atop a rod, which is required for engagement by the jaws of the extensometer. The said disc is preferably the same size as the block and is fixed to the latter by means of a glue of the ARALDITE® type. The hair styling composition to be tested is distributed as uniformly as possible over the surface of each glass disc and is placed for drying such that the surface remains level.

Discs with a surface area of 38 mm2 are used. The amount of composition deposited is 53/c $\mu$g/mm$^2$, c being the dry matter concentration in the composition (in grams per gram of composition). The drying time is 24 hours at 22° C. and a relative humidity of 50%. The rods of the two blocks are positioned in the jaws of the extensometer. The surfaces of the coated discs are subsequently subjected to a compression phase of 3 newtons for 20 seconds by the extensometer. Tension is exerted at a rate of 20 mm/minute for 30 seconds.

The detachment profile is determined by measuring Fmax, corresponding to the maximum tensile force measured with the aid of the extensometer, required to detach the respective surfaces of the two discs. It is preferred to proceed in accordance with the following protocol:

6 pairs of blocks are prepared. For each pair of blocks, a detachment test is carried out in accordance with the procedure indicated above for test 1. The results obtained over the 6 detachment profiles carried out are selected, excluding for each pair of blocks those cases where the styling materials became detached from one of the blocks of the pair. For each remaining detachment profile the Fmax is determined. The mean of these measurements is formed.

Procedure Relating to the Measurement of $E_{s(m/g)}$

The energy provided by the extensometer to bring about the "separation" of the respective surfaces of two rigid and inert, non-absorbent 38 mm$^2$ substrates positioned opposite one another is determined, one of the said substrates consisting of polished glass, whose surface will not be coated with the styling composition, and the other of the said substrates being identical in nature to the substrates defined above; the surface of this substrate is coated with the styling composition; the two surfaces of the said supports are subsequently treated under the same conditions as those of the first procedure, described above, and using an extensometer of the same type as above. Preferably, the protocol used will be as follows 6 Pairs of blocks are prepared. For each pair of blocks, a detachment test is carried out in accordance with the procedure indicated above. The results obtained over the 6 detachment profiles carried out are selected, excluding for each pair of blocks those cases where the styling materials became detached from one of the blocks of the pair. For each remaining detachment profile the $E_{s(m/g)}$ is determined. The mean of these measurements is formed.

The composition according to the invention can comprise other constituents which are conventional in cosmetics, especially preservatives, perfumes, UV filters, active haircare agents, etc. It is understood that the person skilled in the art will know how to select these constituents and their amount in the composition according to the invention so as not adversely to affect its remodellable styling properties.

The compositions according to the invention can be provided in any form known from the prior art which is appropriate for their application to the hair, in particular in the form of a vaporizable composition, mousse, gel, lotion, etc.

The appropriate cosmetically acceptable vehicle is adapted to the method of application selected. The vehicle consists preferably of an appropriate solvent to which may be added additives such as gelling agents, foaming agents, silicones, etc.

It is understood that the person skilled in the art will know how to choose the additional constituents and their amount in the composition according to the invention, such as the constituents of the vehicle, so as not adversely to affect its remodellable styling properties. In particular, he or she will ensure that the Tg of the styling material is less than +10° C. and that the detachment profiles as indicated above are respected.

According to one embodiment of the invention, the composition is a composition vaporizable either by means of a pump or is a pressurized aerosol composition, vaporizable by means of a dispensing valve controlled by a dispensing head, which in turn comprises a nozzle by means of which the aerosol composition is vaporized.

The vaporizable composition according to the invention is a solution or dispersion comprising at least one fixative polymer according to the invention and an appropriate solvent.

Advantageously, the appropriate solvent is water, an alcohol or an aqueous-alcoholic mixture. By alcohol is meant, in accordance with the invention, a $C_1$–$C_4$ aliphatic alcohol, preferably ethanol.

When the vaporizable composition according to the invention is an aerosol composition, it additionally comprises an appropriate amount of propellant.

The propellant consists of the compressed or liquefied gases which are normally employed for the preparation of aerosol compositions. Preference will be given to employing compressed air, carbon dioxide or nitrogen, or else a gas which is soluble or otherwise in the composition, such as dimethyl ether, fluorinated or non-fluorinated hydrocarbons, and mixtures thereof.

The present invention additionally provides an aerosol device consisting of a vessel containing an aerosol composition consisting on the one hand of a liquid phase (or juice) containing at least one styling material as described above in an appropriate solvent and on the other hand a propellant, and a means of dispensing the said aerosol composition.

The present invention additionally provides a method of treating keratinous fibres, especially hair, in which the composition according to the invention as defined above is applied to the said fibres before or after the shaping of the hairstyle.

The present invention additionally provides the use of a composition as defined above in, or for the preparation of, a cosmetic remodellable hair styling formulation.

The present invention additionally provides the use of a polymer as defined above as a styling material, or for producing a styling material, in a remodellable styling formulation.

The examples below allow the invention to be illustrated without, however, seeking to limit its scope.

A number of compositions are produced in the form of lotions.

The compositions are produced with different fixative polymers. Following application to hair and drying, the Tg of the styling material obtained (expressed in ° C.) is measured.

The remodellable styling effect is evaluated on heads for compositions with a dry matter concentration of 4.5% (weight/weight) in an appropriate solvent.

The detachment tests are carried out for the various compositions.

The results are reported in the Tables below.

EXAMPLE 1

Importance of the Tg

| Polymer | Tg (° C.) | Remodellable styling |
|---|---|---|
| AQ 1350 | 0 | Yes |
| HYSTRETCH V43 | −43 | Yes |
| AMERHOLD DR 25 unplasticized (not part of the invention) | +24 | No |
| Neocryl BT 67 (not part of the invention) | +14 | No |

EAMPLE 2

Importance of $F_{max}$

| Polymer | Tg (° C.) | $F_{max}$ (newtons) | Remodellable styling |
|---|---|---|---|
| AQ 1350 | 0 | 23 | Yes |
| HYSTRETCH V43 | −43 | 3.5 | Yes |
| KRATON G1701 (not part of the invention) | −55 | 0.4 | No |

EXAMPLE 3

Importance of $E_{s(m/g)}$

| Polymer | Tg (° C.) | $E_{s(m/g)}$ (μjoules) | Remodellable styling |
|---|---|---|---|
| HYSTRETCH V43 | −43 | 0.1 | Yes |
| ECOCRYL XP 4501 (not part of the invention) | −48 | 900 | No |

| Polymer | Tg (° C.) | E$_{s(m/g)}$ (µjoules) | Remodellable styling |
|---|---|---|---|
| CARBOTAC XPD 1811 (not part of the invention) | −43 | 1200 | No |

| | |
|---|---|
| AQ 1350 | Polyester (marketed by EASTMAN CHEMICAL) |
| HYSTRETCH V-43 | Ethyl acrylate-acrylamide-acrylic acid terpolymer (marketed by GOODRICH) |
| ECOCRYL XP 4501 | Acrylic copolymer (marketed by ATOCHEM) |
| CARBOTAC XPD 1811 | Acrylic copolymer (marketed by GOODRICH) |
| KRATON G 1701 | Styrene-ethylene propylene (37:63) block copolymer (marketed by SHELL CHIMIE) |
| AMERHOLD DR 25 | Ethyl acrylate-methyl methacrylate-acrylic acid-methacrylic acid (marketed by AMERCHOL) |
| KRATON G 1701 | Styrene-ethylene propylene (37:63) block copolymer (marketed by SHELL CHIMIE) |
| Néocryl BT 67 | Acrylic-styrene copolymer (marketed by ZENECA) |

What is claimed is:

1. A remodellable hair styling composition comprising at least one polymer, wherein said at least one polymer is selected such that said composition, after being applied to keratinous fibers and dried thereon, provides a styling material having a glass transition temperature (Tg) of less than +10° C. and a detachment profile defined by
   a) a maximum detachment force $F_{max}$ of greater than 1 newton and
   b) a separation energy $E_{s(m/g)}$ of said styling material placed in contact with a glass surface of less than 300 µJ when said temperature Tg is less than −15° C., and wherein said styling material is present in an effective amount to achieve a remodellable hair styling effect.

2. A composition according to claim 1, wherein said $F_{max}$ is the maximum tensile force, measured using an extensometer, required to detach a surface of a first rigid, inert and non-absorbent substrate from a surface of a second rigid, inert and non-absorbent substrate placed opposite said first substrate wherein said surfaces of said first and second rigid, inert and non-absorbent substrates each have a surface area of 38 mm$^2$ and are coated beforehand with said composition at a rate of 53/c µg/mm$^2$, wherein c is the dry matter concentration in said composition in grams per gram of said composition and wherein said surfaces of said first and second rigid, inert and non-absorbent substrates are dried for 24 hours at 22° C. and a relative humidity of 50%, subjected for 20 seconds to a compressive force of 3 newtons and further subjected for 30 seconds to tension at a rate of 20 mm/minute.

3. A composition according to claim 2, wherein said first and second rigid, inert and non-absorbent substrates are independently chosen from polyethylene, polypropylene, metal alloy and glass.

4. A composition according to claim 1, wherein said seperation energy $E_{s(m/g)}$ is the energy supplied by a extensometer in order to achieve the separation of a surface of a first rigid, inert and non-absorbent substrate from a surface of a second rigid, inert and non-absorbent substrate placed opposite said first substrate, wherein said surfaces of said first and second rigid, inert and non-absorbent substrates each have a surface area of 38 mm$^2$, wherein one of said first and second rigid, inert and non-absorbent substrates comprises polished glass and the other of said substrates is chosen from polyethylene, polypropylene, metal alloy and glass and further wherein both said surfaces are coated with said composition at a rate of 53 µg/c/mm$^2$, c being the dry matter concentration in the composition in grams per gram of composition, and wherein said surfaces of said first and second rigid, inert and non-absorbent substrates are dried for 24 hours at 22° C. and a relative humidity of 50%, subjected for 20 seconds to a compressive force of 3 newtons and further subjected for 30 seconds to tension at a rate of 20 mm/minute.

5. A composition according to claim 4, wherein said $E_{s(m/g)}$ is the work calculated using formula I below:

$$\int_{x_{s1}+0.05}^{x_{s2}} F(x)dx$$

wherein
   F(x) is the force required to produce a displacement (x);
   $x_{s1}$ is a displacement, in millimeters, produced by the maximum tensile force;
   $x_{s2}$ is a displacement, in millimeters, produced by the tensile force which permits total separation of said surfaces of said first and second rigid, inert and non-absorbent substrates.

6. A composition according to claim 1, wherein said at least one polymer is selected from anionic, cationic, amphoteric and nonionic fixative polymers.

7. A composition according to claim 6, wherein said fixative polymers are halogenated.

8. A composition according to claim 7, wherein said fixative polymers are fluorinated.

9. A composition according to claim 1, wherein said at least one polymer is in solubilized form or is a dispersion of solid polymer particles.

10. A composition according to claim 6, wherein said cationic fixative polymers are selected from polymers comprising primary, secondary, tertiary and/or quaternary amine groups which form part of the polymer chain or are linked directly to the polymer chain, said polymers having a weight average molecular weight ranging from 500 to 5,000,000.

11. A composition according to claim 10, wherein said cationic fixative polymers have a molecular weight ranging from 1000 to 3,000,000.

12. A composition according to claim 6, wherein said anionic fixative polymers are selected from polymers comprising groups derived from carboxylic, sulphonic or phosphoric acid, said polymers having a weight-average molecular weight ranging from 500 to 5,000,000.

13. A composition according to claim 12, wherein said anionic fixative polymers are sulphonated polyesters comprising repeating units represented by formula II below:

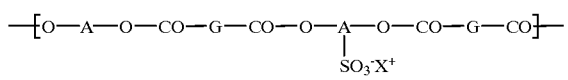

wherein
   A and G are divalent radicals, and
   X is an alkali metal.

14. A composition according to claim 13, wherein said alkali metal is chosen from sodium and potassium.

15. A composition according to claim 13, wherein A is an arylene radical and G is chosen from a cycloalkylene radical and linear or branched alkylene radicals optionally interrupted by one or more oxygen atoms.

16. A composition according to claim 15, wherein said arylene radical is a phenylene.

17. A composition according to claim 15, wherein G is a linear or branched alkylene radical optionally interrupted by one or more oxygen atoms.

18. A composition according to claim 17, wherein G is a (poly)alkylene glycol residue comprising from 1 to 20 alkylene glycol units.

19. A composition according to claim 17, wherein said linear or branched alkylene radical is a lower $C_2$–$C_4$ alkylene radical.

20. A composition according to claim 19, wherein said $C_2$–$C_4$ alkylene radical is an ethylene radical.

21. A composition according to claim 6, wherein said fixative polymers are amphoteric polymers selected from polymers comprising a first unit and a second unit distributed randomly in the polymer chain, wherein said first unit is derived from a monomer containing at least one basic function and said second unit is derived from an acidic monomer containing at least one group chosen from carboxyl and sulpho groups, said first unit and said second unit are chosen from groups derived from zwitterionic carboxybetaine or sulphobetaine monomers, said first unit and said second unit are chosen from cationic polymer chains containing primary; secondary, tertiary or quaternary amine groups, in which at least one of the amine groups carries a carboxyl or sulpho group linked by way of a hydrocarbon radical, or said first unit and said second unit form part of a chain of a polymer having an α,β-dicarboxy ethylene unit in which one of the carboxyl groups has been reacted with a polyamine comprising one or more primary or secondary amine groups.

22. A composition according to claim 21, wherein when said first unit is derived from a monomer containing at least one basic function, said basic function is a basic nitrogen atom.

23. A composition according to claim 6, wherein said nonionic fixative polymers are polyurethanes.

24. A composition according to claim 1, said composition further comprising at least one cosmetic additive.

25. A composition according to claim 24, wherein said at least one cosmetic additive is chosen from plasticizers and neutralizing agents.

26. A composition according to claim 1, wherein said composition is in a form chosen from a vaporizable composition, a mousse, a gel and a lotion.

27. A composition according to claim 1, further comprising a cosmetically acceptable vehicle, wherein said vehicle comprises a solvent to which at least one cosmetic additive may be added.

28. A composition according to claim 27, wherein said at least one cosmetic additive is chosen from gelling agents, foaming agents and silicones.

29. A composition according to claim 27, wherein said solvent is chosen from water, alcohol and an aqueous-alcoholic mixture.

30. A composition according to claim 29, wherein said alcohol is a $C_1$–$C_4$ aliphatic alcohol.

31. A composition according to claim 30, wherein said alcohol is ethanol.

32. A composition according to claim 1, wherein said composition is vaporizable by a pump or is a pressurized aerosol composition.

33. A composition according to claim 32, wherein said composition is an aerosol composition.

34. A composition according to claim 33, wherein said aerosol composition comprises a propellant present in an appropriate amount.

35. A composition according to claim 34, wherein said propellant comprises liquefied or compressed gases.

36. A composition according to claim 35, wherein said gases are chosen from air, carbon dioxide, nitrogen, and gases which are soluble or insoluble in said composition.

37. A composition according to claim 36, wherein said gases which are soluble or insoluble in said composition are chosen from dimethyl ether, fluorinated hydrocarbons and non-fluorinated hydrocarbons.

38. A composition in the form of a rinsable product chosen from shampoos and conditioners, said composition comprising at least one polymer selected such that said composition, after being applied to keratinous fibers, rinsed and dried thereon, leads to a deposit of a cosmetically effective amount of a styling material having a glass transition temperature (Tg) of less than +10° C. and a detachment profile, define by a) a maximum detachment force $F_{max}$ of greater than 1 newton and b) a separation energy $E_{s(m/g)}$ of said styling material placed in contact with a glass surface of less than 300 µJ when said temperature Tg is less than −15° C.

39. An aerosol device comprising a vessel containing an aerosol composition and a means of dispensing said aerosol composition, wherein said aerosol composition comprises a liquid phase comprising, in a cosmetically acceptable solvent, a hair styling composition comprising at least one polymer selected such that said composition, after being applied to keratinous fibers, rinsed and dried thereon, provides a styling material having a glass transition temperature (Tg) of less than +10° C. and a detachment profile, defined by a) a maximum detachment force $F_{max}$ of greater than 1 newton and b) a separation energy $E_{s(m/g)}$ of said styling material placed in contact with a glass surface of less than 300 µJ when said temperature Tg is less than −15° C., and a propellant chosen from liquefied and compressed gases.

40. A method of treating keratinous fibers, comprising applying to said fibers before or after shaping of a hairstyle, a composition comprising: at least one polymer selected such that said composition, after being applied to keratinous fibers and dried thereon, provides a styling material having a glass transition temperature (Tg) of less than +10° C. and a detachment profile, defined by a) a maximum detachment force $F_{max}$ of greater than 1 newton and b) a separation energy $E_{s(m/g)}$ of said styling material placed in contact with a glass surface of less than 300 µJ when said temperature Tg is less than −15° C.

41. A method according to claim 40, wherein said keratinous fibers are human hair.

* * * * *